(12) United States Patent
Beckert et al.

(10) Patent No.: US 8,974,834 B2
(45) Date of Patent: Mar. 10, 2015

(54) METHOD FOR PRODUCING RESERVOIR LAYER FOR HOOF TREATMENT AND RESERVOIR LAYER

(75) Inventors: Iris C. Beckert, Grob-Umstadt (DE); Petra Vogt, Langefeld (DE)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 13/508,891

(22) PCT Filed: Jan. 15, 2010

(86) PCT No.: PCT/IB2010/050200
§ 371 (c)(1),
(2), (4) Date: Jul. 18, 2012

(87) PCT Pub. No.: WO2011/086425
PCT Pub. Date: Jul. 21, 2011

(65) Prior Publication Data
US 2013/0129637 A1  May 23, 2013

(51) Int. Cl.
*A01N 59/06* (2006.01)
*A61K 33/06* (2006.01)
*A61K 47/20* (2006.01)
*A61K 31/11* (2006.01)
*A61K 31/115* (2006.01)
*A61K 31/14* (2006.01)
*A61K 33/26* (2006.01)
*A61K 9/00* (2006.01)
*A61K 45/06* (2006.01)

(52) U.S. Cl.
CPC ............... *A61K 47/20* (2013.01); *A61K 31/11* (2013.01); *A61K 31/115* (2013.01); *A61K 31/14* (2013.01); *A61K 33/06* (2013.01); *A61K 33/26* (2013.01); *A61K 9/0017* (2013.01); *A61K 45/06* (2013.01)
USPC .................................................... 424/682

(58) Field of Classification Search
None
See application file for complete search history.

(56) References Cited

U.S. PATENT DOCUMENTS

| 4,284,611 A | 8/1981 | Gancy et al. |
|---|---|---|
| 5,348,721 A | 9/1994 | Murphy et al. |
| 5,785,862 A | 7/1998 | Graham et al. |
| 5,916,447 A | 6/1999 | Hultén et al. |
| 5,985,234 A | 11/1999 | Dulko |
| 6,036,935 A | 3/2000 | Dulko |
| 6,630,434 B2 | 10/2003 | Besse et al. |
| 2004/0112611 A1 | 6/2004 | Kriesel et al. |
| 2008/0166424 A1 | 7/2008 | Mixon et al. |
| 2009/0110645 A1* | 4/2009 | Morelli et al. .................. 424/43 |

FOREIGN PATENT DOCUMENTS

| GB | 2 250 196 A | 11/1991 |
|---|---|---|
| JP | 2004-501874 | 1/2004 |
| WO | WO 2009/053934 A2 | 4/2009 |

OTHER PUBLICATIONS

Patil, P.K. et al., Immune responses of goats against foot-and-mouth disease quadrivalent vaccine: comparison or double oil emulsion and aluminium hydroxidegel vaccines in eliciting immunity, Vaccine, Jun. 21, 2002, vol. 20, Issues 21-22, pp. 2781-2789.
Casey, W.H., Large Aqueous Aluminum Hydroxide Molecules, Chemical Reviews, 2005, vol. 106, pp. 1-16.
Parker, D.R. and Bertsch, P.M., Identification and Quantification of the $Al_{13}$ Tridecameric Polycation Using Ferron, Environ. Sci. Technol., 1992, vol. 26, pp. 908-914.
Standard Methods for the Examination of Water and Wastewater 20th Edition, ed. Clesceri L.S., Greenberg. A.E.. Eaton, A.D., American Public Health Association, 1998, Washington DC, title page, copyright page, and pp. 3-13—3-31 and 3-44—3-51.
Supplementary International Search Report for EP 10 84 2943, Jun. 20, 2013, 1 page.

* cited by examiner

*Primary Examiner* — Trevor Love
(74) *Attorney, Agent, or Firm* — Merchant & Gould P.C.

(57) ABSTRACT

The present invention provides a kit or article of manufacture comprising as separate components:
(a) a polymeric metal astringent;
(b) an anionic surfactant;
wherein combining component (a) and (b) provides a reaction product of said polymeric metal astringent and said anionic surfactant in form of a precipitate comprising said metal astringent and said anionic surfactant, for use in the preventive and/or therapeutic treatment of hoof or foot disease in cattle and other types of hoofed animals.

12 Claims, No Drawings

METHOD FOR PRODUCING RESERVOIR LAYER FOR HOOF TREATMENT AND RESERVOIR LAYER

CROSS-REFERENCE TO RELATED APPLICATIONS

This application is a 371 of PCT/IB2010/050200 filed Jan. 15, 2010, the entire disclosure of which is incorporated herein by reference in its entirety.

The present invention provides a new kit or article of manufacture for use in the preventive and/or therapeutic treatment of hoof or foot disease in cattle and other types of hoofed animals. The present invention also relates to a method for producing reservoir layer for hoof treatment and reservoir layer used for the treatment and prevention of foot disease in cattle and other types of hoofed animals. More particularly, the present invention relates to the production of a reservoir layer containing metal astringents for the treatment and prevention of diseases concerning hoofes, particularly hairy heel wart disease.

Hairy heel wart disease, also known as Papillomatus Digital Dermatitis (PDD), Digital Dermatitis (DD), strawberry heel warts, or Mortellaro disease, is an infectious disease transmitted among hoofed animals. The disease is manifested as painful skin lesions that form near the junction of the skin and hoof area. In the progressed state, the lesions can produce long hair-like skin growths (papilliforms). The effects of the disease include lameness, loss of weight and decline of general well-being. In the case of dairy cattle, the disease results in a loss of milk production. In some cases, interventive surgery may be required to protect the life of the animal. The disease etiology is recognized as a multivariate problem involving environmental, managerial, and bacterial factors. Exposure to high levels of moisture and manure is likely a significant factor to the disease. In addition, the rapid response to topical antibiotics indicates a bacteriological factor, and *Treponema spirochaete* has been observed in lesions linked to hairy heel wart disease.

Treatment practices for dairy cattle may vary tremendously from farm to farm. Most farms, particularly large dairy operations, may treat the cows multiple times per week to help prevent new cases of hairy heel warts and treat existing infections. Common prophylactic treatments include copper sulfate or formaldehyde with copper sulfate.

Foot baths are commonly used to apply the copper sulfate. After the cows are milked, they are directed to walk through troughs containing a solution of copper sulfate. As more cows move through a foot bath, the trough may become filled with so much soil and organic waste that active components in the foot bath become ineffective, and the trough may even become a vehicle for transferring bacteria between cows. Thus, the foot baths require a significant labor commitment as the solution in the foot bath may need to be replaced frequently. Moreover, these types of foot baths result in high volumes of copper sulfate waste, and in some cases, formaldehyde waste. Copper sulfate is becoming more expensive and the associated environmental concerns continue to increase. There is a need for a system and method of effectively treating and preventing hairy heel wart disease that eliminates the use of copper sulfate, while simultaneously reducing material costs and labor costs.

WO 2009/053934 discloses a method of treating and preventing hairy heel warts (papillomatous digitial dermatitis) in hoofed animals, wherein an aqueous solution comprising a metal astringent including at least one of iron and aluminium is applied to a lower leg and hoof area of an animal to prevent and treat hairy heel wart disease.

The object of the present invention was to provide means for application of an astringent to animals' hoofs which visibly lasts longer than a foamed composition. Further, the object of the present invention was to provide means of a continuous delivery of an astringent to animals' hoofs. In particular, the object of the present invention was to provide means of a continuous delivery of an astringent and an antimicrobial agent to animals' hoofs.

SUMMARY

The present invention provides a kit or article of manufacture comprising as separate components:
(a) a polymeric metal astringent;
(b) an anionic surfactant;
wherein combining component (a) and (b) provides a reaction product of said polymeric metal astringent and said anionic surfactant in form of a precipitate comprising said metal astringent and said anionic surfactant, for use in the preventive and/or therapeutic treatment of hoof or foot disease in cattle and other types of hoofed animals.

In a preferred embodiment the kit or article further comprises an antimicrobial agent.

In a further preferred embodiment the separate compositions (a) and/or (b) are provided as aqueous solution.

Preferably, the present invention provides a kit or article of manufacture comprising as separate compositions:
(a) a first aqueous solution comprising a polymeric metal astringent and an antimicrobial agent;
(b) a second aqueous solution comprising an anionic surfactant;
wherein optionally in addition an antimicrobial agent is comprised, preferably in composition (a).

When combining composition (a) and (b), preferably in the form of the first and second aqueous solution, a reaction product in form of a precipitate is formed comprising said metal astringent and said anionic surfactant. In a preferred embodiment the reaction product comprises an antimicrobial agent.

The present invention therefore provides means for application of an astringent to animals' hoofs which visibly lasts longer than a foamed composition. Further, means are provided for a continuous delivery of an astringent to animals' hoofs. In particular, means are provided for a continuous delivery of an astringent and optionally an antimicrobial agent to animals' hoofs.

A kit or article for use in the treatment of hoof-related diseases, particularly hairy heel warts (papillomatus digital dermatitis), includes preferably an aqueous solution having a metal astringent at a therapeutically effective concentration and an antimicrobial agent and a separate aqueous solution comprising an anionic surfactant.

The metal astringent includes aluminium or iron, and mixtures thereof and is present at least as polymeric species. The metal may include a mixture of monomeric and polymeric species. The polymeric species may be in the form of a polymeric concentrate, such as, for example, polyaluminum chloride or polyferric sulfate. Alternatively, the polymeric species may be formed by partially neutralizing a metal salt. The aqueous solution comprising the metal astringent and optionally the antimicrobial agent is combined with an aqueous solution comprising an anionic surfactant which results in rapid formation of a precipitate which is applied to the lower leg and hoof area of an animal using any known application technique, including, but not limited to, foot baths, foams and spray applications. In preferred embodiments, the two aqueous solutions of the kit of the present invention are mixed and applied using an automated dispensing system. The aqueous solution may include additional components, such as thickeners, to enhance the performance of the metal astringent or contribute additional functionality.

Without being bound to a theory it is believed that the polymeric metal astringent having positive charge due to the metal ions, forms a precipitate by salt formation with the negatively charged anionic surfactant. The reaction product may further contain additional positively or negatively charged counterions. The present inventors found that the precipitate is formed in that way that also other components such as the antimicrobial agent is trapped in the matrix of the precipitate. By that a layer is formed for application of an astringent to animals' hoofs which visible lasts longer than a foamed composition, and which sticks to the hoof and lower leg for an extended time-period. Further, this layer may be considered to represent a reservoir layer which sticks to the hoof and lower leg for an extended time-period and allows continuous delivery of the metal astringent and optionally the antimicrobial agent. The effects of the treatment by using the present invention last longer than if the metal astringent and the antimicrobial agent are applied in form of a foam which is removed, washed off or inactivated by the normal activity of the animal more rapidly than the sticky reservoir layer of the present invention.

In a preferred embodiment of the present invention the polymeric metal astringent includes at least one of iron and aluminium. Further preferred the polymeric metal astringent comprises at least one of polyaluminum chloride, polyaluminum sulfate, polyaluminum chlorosulfate, polyaluminum silicate sulphate, polyaluminum acetate, polyferric chloride, polyferric sulphate, poly-alumino-ferric sulphate and mixtures thereof.

As mentioned above, the aqueous solution comprising the polymeric metal astringent may also contain an antimicrobial agent. The antimicrobial agent preferably comprises at least one of quaternary ammonium compounds (QAC), phenolics, peracids, hydrogen peroxide, acidified sodium chlorite, hypochlorous acid, iodine, chlorhexidine, aldehyde-based germicides such as formaldehyde, glutaraldehyde, alcohols and fatty acids.

In a preferred embodiment the antimicrobial agent is an aldehyde such as formaldehyde or glutaraldehyde. It is particularly preferred that the antimicrobial agent is glutaraldehyde. Further preferred, if glutaraldehyde is used as antimicrobial agent a suitable stabilizer, preferably an alcohol, further preferred isopropanol is also comprised for stabilizing said glutaraldehyde.

As anionic surfactant any anionic surfactant may be used which reacts with the polymeric metal astringent and thereby forms a precipitate. In a preferred embodiment the anionic surfactant may include, but are not limited to, $C_1$-$C_{18}$ alkyl carboxylates, sulfates, and sulfonates. In preferred embodiments, the anionic surfactant are $C_1$-$C_{18}$ alkyl aryl carboxylates, sulfates, or sulfonates. Representative anionic surfactant include, but are not limited to, salicylic acid, sodium cumene sulfonate, sodium toluene sulfonate, sodium xylene sulfonate, sodium dodecyl benzene sulfonate, sodium lauryl sulfate, sodium olefin sulfonate, and mixtures thereof. Further anionic surfactant may include polyoxyethylene or polyoxypropylene $C_8$-$C_{18}$ alkyl ether sulfate, preferably polyoxyethylene or polyoxypropylene $C_{10}$-$C_{16}$ alkyl ether sulfate, further preferred polyoxyethylene or polyoxypropylene $C_{12}$-$C_{14}$ alkyl ether sulfate.

Therefore, according to a preferred embodiment the anionic surfactant is at least one of $C_1$-$C_{18}$ alkyl carboxylates, sulfates, and sulfonates; $C_1$-$C_{18}$ alkyl aryl carboxylates, sulfates, or sulfonates; salicylic acid, sodium cumene sulfonate, sodium toluene sulfonate, sodium xylene sulfonate, sodium dodecyl benzene sulfonate, sodium lauryl sulfate, sodium olefin sulfonate; $C_8$-$C_{18}$ fatty alcohol ether sulfate with 1-5 EO, $C_8$-$C_{18}$ fatty alcohol ether sulphate having 1-5 PO; $C_8$-$C_{18}$ fatty alcohol ether sulphate having 1-5 EO PO and mixtures thereof.

In another preferred embodiment the anionic surfactant is $C_1$-$C_{18}$ alkyl sulfonate or $C_1$-$C_{18}$ alkyl aryl sulfonate.

In a further preferred embodiment the anionic surfactant is $C_8$-$C_{18}$ fatty alcohol ether sulfate with 1-5 EO PO. In a further preferred embodiment the anionic surfactant is $C_{10}$-$C_{16}$ fatty alcohol ether sulfate with 1-5 EO PO, preferably the anionic surfactant is $C_{12}$-$C_{14}$ fatty alcohol ether sulfate with 1-5 EO PO; still further preferred the anionic surfactant is $C_{12}$-$C_{14}$ alkyl ether sulfate with 1-3 EO PO; most preferred the anionic surfactant is $C_{12}$-$C_{14}$ alkyl ether sulfate with 1-3 EO (lauryl ether sulfate). In further preferred embodiments the anionic surfactant may be $C_8$-$C_{18}$ fatty alcohol polyglycol sulfate, $C_{10}$-$C_{16}$ fatty alcohol polyglycol sulfate, or $C_{12}$-$C_{14}$ fatty alcohol polyglycol sulfate.

That is in a preferred embodiment the anionic surfactant is having the formula $CH_3(CH_2)_m CH_2(OC_2H_4)_n$—$OSO_3^- M^+$, wherein m is from 6 to 16, n is from 1 to 5 and $M^+$ is alkali metal ion such as $Na^+$. Preferably m is from 8 to 14, n is from 1 to 5, $M^+$ is alkali metal ion such as $Na^+$. Further preferred m is from 10 to 12; n is from 1 to 5, $M^+$ is alkali metal ion such as $Na^+$.

In another preferred embodiment the anionic surfactant is having the formula $CH_3(CH_2)_m CH_2(OC_2H_4)_n$—$OSO_3^- M^+$, wherein m is from 6 to 16, n is from 1 to 3 and $M^+$ is alkali metal ion such as $Na^+$. Preferably m is from 8 to 14, n is from 1 to 3, $M^+$ is alkali metal ion such as $Na^+$. Further preferred m is from 10 to 12; n is from 1 to 3, $M^+$ is alkali metal ion such as $Na^+$.

In a further particularly preferred embodiment the anionic surfactant is having the formula $CH_3(CH_2)_m CH_2(OC_2H_4)_n$—$OSO_3^- M^+$, wherein m is from 10 to 12; n is 2 or 3, $M^+$ is alkali metal ion such as $Na^+$.

In a further embodiment of the present invention the separate compositions (a) and (b) each are provided as concentrate aqueous solutions having the following concentrations:
(a) in said first aqueous solution: said polymeric metal astringent from 1 to 60 weight-%;
(b) in said second aqueous solution: said anionic surfactant from 1 to 40 weight-%.
wherein optionally an antimicrobial agent is present in a concentration of from 1 to 30 weight-%, preferably in (a).

In a further embodiment of the present invention the separate compositions (a) and (b) each are provided as concentrate aqueous solutions having the following concentrations:
(a) in said first aqueous solution: said polymeric metal astringent from 5 to 50 weight-%;
(b) in said second aqueous solution: said anionic surfactant from 1 to 20 weight-%.
wherein optionally an antimicrobial agent is present in a concentration of from 1 to 30 weight-%, preferably in (a).

In a further embodiment of the present invention the separate compositions (a) and (b) each are provided as concentrate aqueous solutions having the following concentrations:
(a) in said first aqueous solution: said polymeric metal astringent from 10 to 30 weight-%;
(b) in said second aqueous solution: said anionic surfactant from 2 to 15 weight-%.

wherein optionally an antimicrobial agent is present in a concentration of from 1 to 15 weight-%, preferably in (a).

The above mentioned concentrates (a) and (b) are diluted by a factor of 20 to 100 to obtain use solutions which then are combined. This means the use solutions of (a) and (b) contain 1 to 5% of the respective concentrate.

As mentioned above, after combining components (a) and (b) a reaction product in form of precipitate is formed which comprises besides said polymeric metal astringent and said anionic surfactant optionally an antimicrobial agent. Preferably the mixture is dispensed as a foam in which the precipitate is formed as soon as said polymeric metal astringent and said anionic surfactant are combined. This precipitate sticks to a surface, for example when the cows walk through such foam containing the precipitate, on the hoofes and lower leg area of the animal. The precipitate sticks to the hoofes and lower leg area and forms a layer which contains said polymeric metal astringent and said anionic surfactant forming a matrix in which optionally an antimicrobial agent and/or further ingredients may be trapped. As long as metal astringent and optionally the antimicrobial agent and possibly further ingredients contained in the precipitate (i.e. said layer on the hoofes and lower leg of the animal) are able to diffuse from said precipitate or said layer to the hoof or skin of the animal, said layer represents a reservoir layer for continuous delivery of said agents.

The present invention also refers to a paste or gel comprising a reaction product of a polymeric metal astringent and an anionic surfactant for use in the preventive and/or therapeutic treatment of hoof or foot disease in cattle and other types of hoofed animals. The paste or gel preferably further comprises an antimicrobial agent. This paste or gel is useful to be applied to the hoofes and lower leg area for forming said reservoir layer for continuous delivery of the metal astringent and optionally an antimicrobial agent and/or possibly further ingredients contained in said paste or gel. As mentioned above the polymeric metal astringent and the anionic surfactant forms a precipitate which is contained in said paste or gel.

Therefore, the present invention also provides a reservoir layer comprising a reaction product of a polymeric metal astringent and an anionic surfactant for use of said precipitate in the preventive and/or therapeutic treatment of hoof or foot disease in cattle and other types of hoofed animals. In a preferred embodiment the reservoir layer is further comprising an antimicrobial agent.

Preferably the reservoir layer comprises said polymeric metal astringent in a concentration of from 10 to 30 weight %, which represents a metal content of 1 to 10 weight %, said anionic surfactant of from 2 to 15 weight % and optionally and antimicrobial agent from 1 to 15 weight % of the wet weight of the reservoir layer.

The present invention also provides a method for preparing a reservoir layer comprising a reaction product of a polymeric metal astringent and an anionic surfactant by combining a polymeric metal astringent and an anionic surfactant. In a preferred embodiment the reservoir layer comprises an antimicrobial agent. Preferably, the reservoir layer comprising the metal astringent and the anionic surfactant is prepared by combining a first aqueous solution comprising a polymeric metal astringent and optionally an antimicrobial agent, and a second aqueous solution comprising an anionic surfactant.

The method comprises formation of a precipitate upon combining said components, preferably by combining said first and said second aqueous solution. Further preferred a propellant is added in order to provide a foam which is containing the precipitate.

Further, the method preferably comprises the application of the resulting precipitate onto the hoof and/or lower leg of hoofed animals for the preventive and/or therapeutic treatment of hoof or foot disease in cattle and other types of hoofed animals.

The present invention also provides a kit, an article or a composition for use in the preventive and/or therapeutic treatment of hoof or foot disease in cattle and other types of hoofed animals comprising the kit or article according to the present invention, the paste or gel according to the present invention, the reservoir layer according to the present invention or the reservoir layer prepared by the method according to the present invention.

Further, the present invention provides a method for preventive and/or therapeutic treatment of hoof or foot disease in cattle and other types of hoofed animals by applying a reaction product of a polymeric metal astringent and an anionic surfactant. The reaction product optionally comprises an antimicrobial agent. Further, the reaction product is in form of a precipitate which is formed by combining a polymeric metal astringent, an anionic surfactant and In a preferred method for preventive and/or therapeutic treatment of hoof or foot disease in cattle and other types of hoofed animals the precipitate is formed by combining the following separate compositions:
(a) a first aqueous solution comprising a polymeric metal astringent and optionally an antimicrobial agent;
(b) a second aqueous solution comprising an anionic surfactant.

In a preferred method the precipitate is applied onto the hoofes or lower leg of the respective animal.

Preferably, the method is for preventive and/or therapeutic treatment of hoof related diseases, particularly hairy heel warts (papillomatus digital dermatitis).

DETAILED DESCRIPTION

A kit or article of manufacture and method is described herein for use in treating and preventing hoof related diseases in cows and other hoofed animals or ungulates, including sheep, pigs horses and camels, particularly hairy heel warts (papillomatus digital dermatitis. The kit or article of manufacture includes at least two different components to be mixed. This system of at least two components a) and b) contain: a) a polymeric astringent metal salt, preferably in an aqueous solution and b) an anionic surfactant, preferably in an aqueous solution. The astringent metal salt, such as aluminum and/or iron, is present in a therapeutically effective amount in the aqueous use solution. According to the present invention the metal astringent is present in its polymeric form. Under some conditions, the astringent metal may form a mixture of polymeric and monomeric species.

Astringent agents promote a precipitation of proteins on a skin's surface and may be used to stop or slow down bleeding and promote drying out of lesions. This disclosure focuses on trivalent metal ion astringents, particularly aluminum and iron, for the treatment and prevention of hairy heel wart disease. The polycationic metal ions likely promote cross linking and precipitation of proteins through ionic interactions. This cross linking may toughen the skin against the macerating effects of moisture and manure that may be the prelude to new infections, as well as promote the drying up and inactivation of existing lesions. Thus, the chemistry of these metal ions is well-suited for both the treatment and prevention of hairy heel wart disease. In preferred embodiments, the astringent metals comprise salts in which the metal ion and the corresponding ligand are only weakly associated in the aqueous solution. Metal hydrates are formed that can then be partially neutralized to form metal hydroxide poloxocations with high polycationic states.

The metal astringent agents are derived from aluminum, iron and combinations of aluminum and iron. Aluminum astringent agents include, but are not limited to, aluminum behenate, aluminum benzoate, aluminum bromohydrate, aluminum chloride, aluminum chlorohydrate (also known as polyaluminum chloride), aluminum dichlorohydrate, aluminum sesquichlorohydrate, aluminum hydroxide, aluminum citrate, aluminum formate, aluminum glycolate, aluminum glycinate, aluminum lactate, aluminum nitrate, aluminum phosphate, sodium aluminum phosphate, aluminum propionate, aluminum subpropionate, aluminum stearate, aluminum sulfate, ammonium, potassium aluminum sulfate, sodium aluminum sulfate, aluminum acetate (Burow's solution), aluminum subacetate, aluminum chlorohydrex polyethylene glycol, aluminum chlorohydrex propylene glycol, aluminum dichlorohydrex polyethylene glycol, aluminum dichlorohydrex propylene glycol, aluminum sesquichloroghydrex polyethylene glycol, aluminum sesquichlorohydrex propylene glycol, aluminum zirconium octachlorohydrate, aluminum zirconium octachlorohydrex gly, aluminum zirconium pentachlorohydrate, aluminum zirconium pentachlorohydrex gly, aluminum zirconium tetrachlorohydrate, aluminum zirconium tetrachlorhydrex gly, aluminum zirconium trichlorhydrate, aluminum trichlorohydrex gly, polyaluminum sulfate, polyaluminum sulfate chloride, polyaluminum ferrisulfate, polyaluminum ferrisulfate chloride, polyaluminum ferrichloride, polyaluminum sulfate silicate, and mixtures thereof.

As stated above, it is preferred to use an aluminum agent where the ligand (for example, chloride) weakly binds to the metal when the astringent is in an aqueous solution. Preferred aluminum astringent agents include, but are not limited to, aluminum chloride, aluminum sulfate, sodium aluminum sulfate, potassium aluminum sulfate, aluminum acetate, aluminum subacetate, aluminum lactate, or any polyaluminum species. Aqueous concentrates of aluminum sulfate and various polyaluminum salts are commonly used in the water treatment industry and are commercially available.

Iron astringent agents include, but are not limited to, ferric chloride, ferric ammonium citrate, ferric ammonium sulfate, ferric sulfate, ferric subsulfate (Monsel's solution), ferric citrate, ferric lactate, ferric nitrate, ferric orthophosphate, ferric phosphate, ferric pyrophosphate, ferric tartrate, polyferric chloride, polyferric sulfate, and mixtures thereof. Preferred iron astringent agents include, but are not limited to, ferric chloride, ferric sulfate, ferric subsulfate, polyferric chloride, polyferric sulfate, and mixtures thereof.

An appropriate concentration of the metal astringent in the aqueous solution (use solution) is from 0.01 to 10 weight percent, and a preferred concentration is from 0.1 to 5.0 weight percent. This measure to quantify the metal astringent in the aqueous solution considers the concentration of the astringent agent (i.e. the metal and the ligand that it binds to; for example, aluminum acetate or aluminum sulfate). An appropriate concentration of the metal content in the aqueous solution (use solution) is from 0.01 to 1.5 weight percent. As an example, a concentrated aqueous solution containing 24 weight percent of polyaluminum chloride (dialuminum chloride pentahydroxide ($Al_2ClH_{10}O_5$)) has an aluminum content of approximately 7 weight percent and the respective use solution (dilution by 1:100) has an aluminium content of approximately 0.07 weight percent. As described below, in preferred embodiments, the aqueous solution is prepared by diluting a concentrate of the metal astringent. The concentrate may be in the form of a powder, a tablet, dispersion or liquid.

In the present invention the metal astringent in the aqueous solution comprises polymeric species. The polymeric species also may be referred to as polynuclear or metal hydroxide poloxocations. Reference is made to Casey, W. H., Large Aqueous Aluminum Hydroxide Molecules, Chemical Reviews, 2005, vol. 106, pp. 1-16 for additional background on polymeric species. In aqueous solutions, aluminum may form hydrates and polyaluminum species. These polyaluminum species, such as polyaluminum chloride, polyaluminum sulfate, and polyaluminum chlorosulfate, are used for water treatment in order to provide the greatest efficiency to coagulate and settle out suspended materials in drinking water. These highly cationic complexes may also promote greater protein precipitation due to a greater number of ionic sites for interaction. These polymeric systems comprise a plurality of polymer species depending on the manufacturing process and an age of the polymeric system. The system may include well characterized species such as, for example, $Al_{13}^{7+}$ tridecamer $Al_{12}(OH)_{24}AlO_4(H_2O)_{12}^{7+}$ and $Al_{30}^{18+}$ ($Al_2O_8Al_{28}(OH)_{56}(H_2O)_{26}^{18+}$), which are identifiable using techniques such as nuclear magnetic resonance spectroscopy and x-ray crystallography.

In one embodiment, the polyaluminum species may be formed by increasing the pH and partially neutralizing an aqueous solution of an aluminum salt. Increasing the basicity of the aqueous solution results in a greater percentage of the polyaluminum species. However, if the conditions of the aqueous solution are too basic, poorly soluble aluminum hydroxide is formed. In a preferred embodiment, a pH level of the aqueous solution is between 4.0 and 6.0, in order to maximize a percentage of polyaluminum species in the aqueous solution.

Whereas, the precipitate formed by combining the polymeric metal astringent and the anionic surfactant is stable at a pH from approximately pH 4.4 to pH 12.

In a preferred embodiment dialuminum chloride pentahydroxide is used as metal astringent in this invention. Besides that, other commonly recognized aluminum astringents are aluminum sulfate and aluminum acetate. Aluminum acetate is reported in the Code of Federal Regulations as being an astringent active ingredient at concentrations ranging between 0.13 and 0.5 percent, whereas aluminum sulfate is reported at concentrations of 46 to 63 percent. (See 21 C.F.R. 347.) As such, aluminum acetate (i.e. Burow's solution) likely has a greater weight efficiency than aluminum sulfate. While not wishing to be bound by theory, it is believed that aluminum acetate may more easily form these polyaluminum species, compared to aluminum sulfate, and thus a lower concentration of aluminum acetate may be sufficient as an astringent. However, it is recognized that aluminum sulfate, at certain conditions, may also form polyaluminum species.

Partially neutralized solutions of aluminum may be described and classified by the molar ratio of hydroxide [OH] and aluminum [Al] (i.e. R is equal to [OH]/[Al]). For purposes here, a maximum value of R is generally less than three since at R equal to three a precipitate of $Al(OH)_3$ forms. A suitable range of R is between approximately 0.2 and 2.7, in order to maintain an aqueous solution, and a preferred range of R is between approximately 1.0 and 2.5. At these ratios, at least some of the aluminum species in the aqueous solution is polymeric or polynuclear.

Many polyaluminum products may be described by an R value and/or a basicity percentage [(R/3)*100%]. For example, a coagulant of polyaluminum chloride used in the water treatment industry has a basicity of approximately 83-84 percent and an R value of approximately 2.49-2.52. An alternative composition of polyaluminum chloride has a basicity of approximately 50 percent and an R value equal to approximately 1.5 Similarly, a coagulant of polyaluminum chlorosulfate has a basicity of approximately 50 percent and an R value of approximately 1.5.

An aqueous solution containing polyaluminum may be formed using at least two different methods. In one embodiment, a polyaluminum concentrate, such as, for example, polyaluminum chloride (aluminum chlorohydrate), may be diluted to form an aqueous solution of polyaluminum. In an alternative embodiment, as described above, an aluminum salt may be diluted and combined with an alkalinity source to form the polyaluminum species in situ. Reference is made to U.S. Pat. No. 5,348,721 and U.S. Pat. No. 5,985,234, both of which disclose the formation of polyaluminum chlorosulfates for use in water treatment. Also see U.S. Pat. No. 4,284,611 and U.S. Pat. No. 6,036,935 for additional background on the formation of polyaluminum solutions.

Similar to aluminum, iron may also form a mixture of monomeric and polymeric species in an aqueous solution, under certain conditions. Commercially available coagulants used in drinking water include polyferric chloride and polyferric sulfate. As also described above for aluminum, a polyferric species may be formed by partially neutralizing a ferric salt. See U.S. Pat. No. 5,785,862 and U.S. Pat. No. 5,916,447, which both describe the formation of polymeric iron for the water treatment industry.

Solutions of iron may also be classified by the molar ratio of hydroxide [OH] and iron (i.e. R is equal to [OH]/[Fe]). A suitable R range for aqueous solutions containing iron is between approximately 0.1 and 0.5, and a preferred value is approximately 0.3. As stated above, an example of a commercially available product is polyferric sulfate having an R value of 0.3 and a basicity of approximately 10 percent.

An aqueous solution also may be a mixture of polyaluminum, polyferric species, and poly-alumino-ferric species.

In most cases, the metal astringent in an aqueous solution is a mixture of monomeric and polymeric species. The quantification of aluminum and iron species can be measured using the standard ferron assay. For example, three classes of aluminum species, $Al_a$ for monomeric aluminum, $Al_b$ for medium sized polyaluminum species, and $Al_c$ for large polyaluminum species, are quantified based on the reaction time with the ferron dye. The ferron dye is believed to react rapidly and irreversibly with the monomeric metal, whereas polymeric forms of the metal take longer to react depending on their size. The standard convention is to quantify $Al_a$ (monomeric aluminum) by the reaction that occurs in the initial 3 minutes, $Al_b$ (medium sized polymeric species) by the reaction that occurs between 3 minutes and 30 minutes, and $Al_c$ (large polymeric species) by the difference between the total aluminum content and $Al_a+Al_b$. Reference is made to D. R. Parker, P. M. Bertsch, Identification and Quantification of the Aln Tridecamer Polycation Using Ferron, Environ. Sci. Technol. 1992, vol. 26, pp. 908-914 for additional background on using the ferron assay for speciation of a metal. For our purposes, polyaluminum is defined by $Al_b$ and $Al_c$. Other techniques that may be used to classify the speciation of the metal include nuclear magnetic resonance spectroscopy, size exclusion chromatography, and x-ray crystallography. Total aluminum content can be determined by atomic adsorption or inductively coupled plasma. Reference is made to Standard Methods for the Examination of Water and Wastewater 20th Edition, ed. Clesceri L. S., Greenberg A. E., Eaton A. D. American Public Health Association, 1998, Washington D.C.

In some embodiments, aluminum and iron may be used in combination in an aqueous solution, and both the aluminum and the iron may form polymeric species. The pH of the aqueous solution is preferably between approximately 4.0 and 6.0 to optimize formation of the polyaluminum and polyferric species, which are believed to be a significant contributor to the astringent affect of the metals. The aqueous solution may be classified based on a weight percent of the aluminum and/or iron that is in polymeric form, based on results from the ferron assay. A suitable amount of the polymeric species, which includes aluminum, iron and mixtures thereof, is equal to or greater than approximately 10 weight percent of the total metal in the solution. A preferred range of the polymeric species is between approximately 25 and 95 weight percent of the total metal, and more preferably between approximately 50 and 95 weight percent.

As discussed above, aluminum forms polynuclear or polymeric species in an aqueous solution, under specific conditions. At a pH of 4.1, the aluminum acetate (Burow's solution) most likely contained a mixture of polymeric and monomeric aluminum species. It is believed that the polyaluminum species are responsible, in part, for the performance of the aluminum acetate in treating the lesions.

Concentrates and Optional Components

In some embodiments, the aqueous solution (a) containing the polymeric metal astringent is formed from one or more concentrates to be diluted with water near the time of use, i.e. before being combined with the anionic surfactant. The concentrate may be in the form of a solid powder, tablet, dispersion or liquid. The metal astringent concentrate may be used alone or in combination with other components. For example, the aqueous solution may be formed by a combination of two concentrates that are mixed together and diluted with water. In that case, a first concentrate may contain the metal astringent and a second concentrate may contain an antimicrobial agent and optionally one or more further components.

Examples of further components include, but are not limited to surfactants (cationic or non-ionic), skin conditioners and buffering agents, as discussed further below. In some cases it may be preferred to use a two concentrate system for preparing the aqueous solution containing the polymeric metal astringent, if for example some of the materials do not have long-term compatibility when mixed together. Also, a two-concentrate system provides greater flexibility to use different formulations of enhancing components, as desired or as necessary. In preferred embodiments, the first concentrate of the metal astringent is highly concentrated such that the user is able to use small quantities to form the aqueous solution. In preferred embodiments, the first concentrate is a liquid for ease of use.

In some embodiments, the aqueous solution containing the polymeric metal astringent (a) also contains a surfactant (cationic or non-ionic), which enables the aqueous solution to wet and spread over the skin by reducing the surface tension of the aqueous composition. Antimicrobial surfactants may be used to achieve the reduced surface tension while also offering antimicrobial properties. Cationic or non-ionic surfactants may be used as such surfactants since they are compatible with the highly cationic astringent salts. A suitable concentration of the surfactant in the aqueous solution is between approximately 0.05 and 1.0 weight percent. Once the aqueous solution (a) is brought into contact with the aqueous solution (b) comprising the anionic surfactant a precipitate is formed.

In some embodiments, the aqueous solution (a) or (b) or both includes a thickener to increase viscosity and retain a greater quantity of liquid on the skin's surface. Thickeners, or thickening agents, may include, but are not limited to, cellulosic thickeners (such as hydroxyethylcellulose, xanthan gum, and carboxymethylcellulose), surfactant thickened systems, associative thickeners, clays and silicas. When a thickener is present, the composition may possess thixotropic properties of increased viscosity with decreasing shear. This may reduce misting effects with spraying or increase solution retention on the surface.

In some embodiments, the aqueous solution is thickened by a surfactant thickened system comprising a combination of surfactant components to impart rod-like micelle properties (thickening via dilution). Reference is made to U.S. Pat. No. 6,630,434, which is assigned to Ecolab Inc., the assignee of this application. Here a low viscosity aqueous composition is described which provides increasing viscosity upon dilution which provides a high viscosity diluted composition.

Cationic surfactants may include, but are not limited to, nitrogen containing amines, trialkylamines, amines having one or two alkyl groups and correspondingly two or one alkylene oxide groups, preferably ethylene oxide groups. Commonly available quaternary ammonium compounds can be used wherein the quaternary ammonium compound is made from aliphatic amines, aromatic amines or alkyl substituted aromatic amine substituents and trialkylamine oxides. Preferred quaternary ammonium surfactants include, but are not limited to, $C_{12}$-$C_{18}$ alkyl trimethyl ammonium salts, $C_{12}$-$C_{18}$ alkylpyridinium salts of chloride, bromide, iodide, sulfate, and methosulfate. Typical examples include, but are not limited to, myristyl trimethyl ammonium bromide, cetyl trimethyl ammonium chloride, cetylpyridinium chloride, stearyl trimethyl ammonium chloride, tallow trimethyl ammonium chloride, and mixtures thereof. Preferred amine oxide surfactants include $C_{12}$-$C_{18}$ alkyl dimethyl amine oxides and N,N-bis(2-hydroxyethyl) $C_{12}$-$C_{18}$ alkyl amine oxides. Representative materials include, but are not limited to, lauryl dimethyl amine oxide, N,N-bis(2-hydroxyethyl) cocamine oxide, myristyl dimethyl amine oxide, cetyl dimethyl amine oxide, oleyl dimethyl amine oxide, stearyl dimethyl amine oxide, tallow dimethyl amine oxide, N,N-bis(2-hydroxyethyl)lauryl amine oxide, N,N-bis(2-hydroxyethyl) myristyl amine oxide, N,N-bis(2-hydroxyethyl)myristyl amine oxide, N,N-bis(2-hydroxyethyl)myristyl amine oxide, N,N-bis(2-hydroxyethyl)cetyl amine oxide, N,N-bis(2-hydroxyethyl)tallow amine oxide, and mixtures thereof. Preferred amine surfactants include, but are not limited to, $C_{12}$-$C_{18}$ alkyl dimethyl amines, N,N-bis(2-hydroxyethyl) $C_{12}$-$C_{18}$ alkyl amines, and N,N-bis(2-hydroxypropyl) $C_{12}$-$C_{18}$ alkyl amines. Typical examples include, but are not limited to, lauryl dimethyl amine, myristyl dimethyl amine, cetyl dimethyl amine, oleyl dimethyl amine, stearyl dimethyl amine, tallow dimethyl amine, N,N-bis(hydroxyethyl)myristyl amine, N,N-bis(hydroxyethyl)cetyl amine, N,N-bis(hydroxyethyl)oleyl amine, N,N-bis(hydroxypropyl)oleyl amine, N,N-bis(hydroxypropyl)tallow amine, and mixtures thereof.

The aqueous solution may also optionally comprise additional components configured to improve the performance of the metal astringent or to contribute additional functionality to the end product. For example, the composition may include skin conditioners, such as glycerin, propylene glycol, sorbitol, lanolin, derivates of polyethylene glycol (PEG)-lanolin and polypropylene glycol (PPG)-lanolin, aloe vera, and allantoin, to promote skin health and healing. Buffering agents may be used to adjust pH and control the speciation of the metal astringents. Buffers may include organic acids, such as monocarboxylates, phosophoric acid, carbonates, and similar products. The pH may be adjusted by adding alkalinity such as sodium bicarbonate, sodium carbonate, sodium hydroxide and potassium hydroxide. Film forming polymers may be used in the aqueous solution to hold residual active materials on the skin surface. The film forming polymers may include polyethylene glycol resins, polyvinyl alcohol, polyacrylates, polyvinyl pyrrolidinone, polyurethanes and corresponding copolymers.

Colorants selected from generally recognized dyes and pigments employed in food, drug and cosmetic formulations may be part of the composition. Organic astringents such as witch hazel, tannins and tea tree oil may be used as well. Any of these optional components may be used in various combinations depending on the desired features of a particular product.

As stated above, the aqueous solution comprising the polymeric metal astringent (a) may be formed by combining at least two concentrates together and diluting with water. A first concentrate may contain the metal astringent and optionally at least one of further optional components described above. A second concentrate may include at least an antimicrobial agent and optionally at least one of further optional components described above.

The other mandatory component (b) comprising the anionic surfactant may be provided as a solid or preferably as aqueous concentrate.

The concentrates are sold as a kit, comprising at least two components: (a) a concentrate containing the polymeric metal astringent and (b) a concentrate containing the anionic surfactant. The kit may include instructions for diluting the concentrates to prepare aqueous use solutions and to combine the aqueous solutions made from (a) and (b) to form the precipitate according to the present invention. The instructions may also include instructions for forming a solution having a specific concentration of the metal and/or instructions to adjust a pH level of the aqueous solution to control speciation of the metal. In another example, the instructions may include instructions on forming a foam solution having a specific foam density.

EXAMPLES

Example 1

Formation of a Precipitate with an Anionic Surfactant (Texapon®NSO) and Chemical Analysis Thereof 50 ml of an aqueous solution (a) containing approximately 31.5 weight % polyaluminium chloride (dialuminum chloride pentahydroxide), 7% glutaraldehyde was mixed with 10 g Texapon®NSO ($C_{12}$-$C_{14}$ alkyl ether sulfate with 2 mole EO). Before mixing the aluminium content of the aqueous solution (a) was about 9.5 weight %. Upon combination a white solid was immediately formed which separated from the clear solution. The white precipitate was analyzed with respect to its contents of glutaraldehyde, Texapon®NSO. The content of polyaluminium chloride was analyzed by the content of Al-ions by XRF. The results are shown in table 1.

TABLE 1

Analysis of the precipitate

| compound | theoretical values based on the formulation | quantified values |
|---|---|---|
| Texapon ® NSO | 16.6% | 12.1% |
| glutaraldehyde | 5.8% | 3.7 |
| Al | 7.9% | 8.4 |

The experiment shows that by combining polyaluminum chloride with an anionic surfactant (here $C_{12}$-$C_{14}$ alkyl ether sulfate with 2 mole EO) a precipitate is formed which also contains the antimicrobial agent glutaraldehyde in significant amounts.

Example 2

Formation of a Precipitate with an Anionic Surfactant (Sulfonate)

50 ml of an aqueous solution (a) containing 10% polyaluminium chloride and 7% glutaraldehyde was mixed with 50 ml of an aqueous solution (b) containing 10 weight % dodecylbenzenesulphonic acid. Before mixing the aluminium content of the aqueous solution (a) was about 3 weight %. Upon mixing a white solid immediately was formed which separated from the clear solution.

This experiment confirmed that the precipitate observed was due to combination of anionic surfactants with polyaluminium chloride.

Comparative Example 3

Formation of a Precipitate with a Cationic Surfactant (Barquat®DM-50)

50 ml of an aqueous solution (a) containing 10% polyaluminium chloride, 7% glutaraldehyde was mixed with 50 ml of an aqueous solution (b) containing 10 weight % N-alkyl($C_{12}$-$C_{16}$)-N-benzyl-N,N-dimethylammonium chloride (Barquat®DM-50). The mixture remained clear and no precipitate was formed. This experiment confirmed that the precipitate observed was due to combination of anionic surfactants with polyaluminium chloride and that the addition of cationic surfactants did not achieve this effect.

Example 4

Application of the Composition of the Present Invention to Lower Legs and Hoofes The composition of the present invention was applied as a foam to the lower legs and hoofes of cows. For this a 5% use solution (a) prepared from a concentrate containing 30% polyaluminum chloride and 7% glutaraldehyde and a 5% use solution (b) prepared from a concentrate containing 7% by weight Texapon®NSO ($C_{12}$-$C_{14}$ alkyl ether sulfate with 2 mole EO) was combined and foamed. A foam was formed that contained a precipitate. The foam was filled in a tub through which the cows walked. The foam sticked very well and remained about 1 to 2 days on the cow's lower leg and hoofes. Apart from the long lasting active foam on the lower leg and hoofes, it was observed that the foam broke down on the leg to form a rather strong and dry layer on the skin and the claw horn which lasted for about 1 to two days. This layer had the consistency of a soft, air permeable barrier which did not hinder the joints or induce tension on the subjacent skin. The barrier forming layer turned out to be useful to dry the skin and to protect the leg from soiling. The fresh and active foam disinfected the claw, delivered astringency to the skin and provided a horn hardening effect as well as a longer lasting protective layer.

In phase I the animals were treated every day for one week. In phase II the animals were treated 3 times a week. Phase I was directly followed by phase II without interruption. The foam containing the precipitate of the present invention was filled in a tub through which the cows walked.

A group of a total of 1045 cows were treated of which 49 animals had lesions. The total number of cows infected with digital dermatitis decreased during the treatment with the composition of the present invention in phase I from 4 to 3, whereby no new lesions occurred. Whereas the total number of cows infected with digital dermatitis during the treatment using comparative product A decreased only from 3 to 2 with no new lesion occurring; and the total number of cows infected with digital dermatitis during the treatment using comparative product B increased from 2 to 3, with 2 new lesions occurring.

Results of phase II: 5 animals newly infected with digital dermatitis were healed after phase II using the composition of the present invention. All lesions were dried, inactive and turned grayish. Only 2 cows were newly infected with digital dermatitis during phase II, which means a reduction of the rate of new infections by using the composition of the present invention.

The invention claimed is:

1. A kit comprising as separate components:
   (a) a polymeric metal astringent at a concentration of from 5 to 50 weight % and an antimicrobial agent;
   (b) an anionic surfactant at a concentration of from 2 to 15 weight %;
   wherein components (a) and (b) are selected such that combining component (a) and (b) provides a reaction product of said polymeric metal astringent and said anionic surfactant in the form of a precipitate comprising said metal astringent and said anionic surfactant, for use as a reservoir layer comprising the reaction product in the preventive and/or therapeutic treatment of hoof or foot disease in cattle and other types of hoofed animals.

2. The kit of claim 1, wherein the separate components (a) and (b) are provided as aqueous solutions.

3. The kit of claim 1, wherein the polymeric metal astringent includes at least one of iron or aluminium.

4. The kit of claim 1, wherein the polymeric metal astringent comprises at least one of polyaluminum chloride, polyaluminum sulfate, polyaluminum chlorosulfate, polyaluminum silicate sulphate, polyaluminum acetate, polyferric chloride, polyferric sulphate, poly-alumino-ferric sulphate and mixtures thereof.

5. The kit of claim 1, wherein the antimicrobial agent comprises at least one of quaternary ammonium compounds (QAC), phenolics, peracids, hydrogen peroxide, acidified sodium chlorite, hypochlorous acid, iodine, chlorhexidine, aldehyde-based germicides such as formaldehyde, glutaraldehyde, alcohols or fatty acids.

6. The kit of claim 1, wherein the antimicrobial agent is an aldehyde.

7. The kit of claim 1, wherein the anionic surfactant is at least one of $C_1$-$C_{18}$ alkyl carboxylates, sulfates, and sulfonates; $C_1$-$C_{18}$ alkyl aryl carboxylates, sulfates, or sulfonates; salicylic acid, sodium cumene sulfonate, sodium toluene sulfonate, sodium xylene sulfonate, sodium dodecyl benzene sulfonate, sodium lauryl sulfate, sodium olefin sulfonate; C8-C18 fatty alcohol ether sulfate with 1-5 EO, $C_8$-$C_{18}$ fatty alcohol ether sulphate having 1-5 PO; $C_8$-$C_{18}$ fatty alcohol ether sulphate having 1-5 EO PO or mixtures thereof.

8. The kit of claim 1, wherein the anionic surfactant is $C_8$-$C_{18}$ fatty alcohol ether sulfate with 1-5 EO PO.

9. The kit of claim 1, wherein the anionic surfactant is $C_1$-$C_{18}$ alkyl sulfonate.

10. The kit of claim 1, wherein the anionic surfactant is $C_1$-$C_{18}$ alkyl aryl sulfonate.

11. The kit of claim 1, wherein the precipitate further comprises the antimicrobial agent.

12. The kit of claim 1, wherein component (a) further comprises 1 to 15 weight % of an antimicrobial agent.

* * * * *